US00PP36783P2

(12) United States Plant Patent
Rosas et al.

(10) Patent No.: US PP36,783 P2
(45) Date of Patent: Jul. 1, 2025

(54) STRAWBERRY PLANT NAMED 'PLARED 19140'

(50) Latin Name: ***Fragaria* x *ananassa***
Varietal Denomination: Plared 19140

(71) Applicant: Plantas de Navarra S.A., Valtierra (ES)

(72) Inventors: Manuel Rosas, Anderson, CA (US); Craig Gaines, Anderson, CA (US)

(73) Assignee: Plantas de Navarra S.A., Valtierra (ES)

( * ) Notice: Subject to any disclaimer, the term of this patent is extended or adjusted under 35 U.S.C. 154(b) by 0 days.

(21) Appl. No.: 18/445,240

(22) Filed: Jun. 13, 2023

(51) Int. Cl.
*A01H 5/08* (2018.01)
*A01H 6/74* (2018.01)

(52) U.S. Cl.
USPC ..... Plt./209
CPC ..... *A01H 6/7409* (2018.05)

(58) Field of Classification Search
USPC ..... Plt./209
CPC ..... A01H 6/7409; A01H 5/08
See application file for complete search history.

(56) References Cited

U.S. PATENT DOCUMENTS

PP20,552 P3 12/2009 Shaw et al.

*Primary Examiner* — Keith O. Robinson
(74) *Attorney, Agent, or Firm* — Hunt IP Law

(57) ABSTRACT

The new and distinct variety of strawberry plant named 'Plared 19140' is provided. The variety can be distinguished by its outstanding features of larger and redder fruit, position of achenes inserted into the fruit, and increased production of summer planting using frigo plants.

4 Drawing Sheets

Latin name of the genus and species:
Botanical classification:
a. Genus—*Fragaria.*
b. Species—x *ananassa.*
Variety denomination: The new strawberry plant claimed is of the variety denominated 'Plared 19140'.

BACKGROUND OF THE INVENTION

Field of the Invention

The present invention relates to a new and distinct annual variety of strawberry plant, which has been given the variety denomination of 'Plared 19140'.

Background of the Related Art

Cultivated strawberry is a hybrid species of the genus *Fragaria* that is grown worldwide for its fruit. Modern strawberry was first bred in Brittany, France, in the 18$^{th}$ century by crossing *Fragaria virginiana* with *Fragaria chilonesis*. Strawberry fruit is an aggregate accessory fruit, with the fleshy part of the fruit being derived from the receptacle that holds the ovaries.

Strawberry varieties vary widely in color, size, shape, flavor, season of ripening, degree of fertility, and susceptibility to disease. Certain varieties vary in foliage, and some vary in the relative development of their reproductive organs. Typically, strawberry flowers appear hermaphroditic in structure, but function as either male or female. Generally, commercial production of strawberry plants involves propagation from runners and distribution as either plugs or bare root plants. Cultivation is either perennial or annual plasticulture. During the off season, strawberries can also be produced in greenhouses.

Strawberry fruit is widely appreciated for its characteristic bright red color, aroma, juicy texture, and sweetness. Strawberry fruit is a popular fruit that is generally consumed either fresh or in prepared foods, such as preserves and baked goods.

Strawberries are an important and valuable fruit crop. Accordingly, there is a need for new varieties of strawberry plants. In particular, there is a need for improved varieties of strawberry plant that are stable, high yielding, and agronomically sound.

SUMMARY OF THE INVENTION

The present invention relates to a new and distinct annual variety of strawberry, which has been given the variety denomination of 'Plared 19140'. Its market class is that of fresh fruit. 'Plared 19140' can be intended for use as a frigo plant to be planted in the summer and to produce fresh fruit in the fall and beyond.

The new strawberry variety is a selection resulting from a sexual cross of strawberry plants in Watsonville, California in 2019, involving a seed parent known as '15-097R' (unpatented) and a pollen parent known as '16-54R' (unpatented).

The selection was subsequently evaluated for four years in Watsonville, California.

Asexual reproduction of the new variety by cutting propagation since 2019 in Watsonville, CA has demonstrated that the new variety reproduces true to type with all of the morphological characteristics, as herein described, firmly fixed and retained through successive generations of such asexual propagation.

Selection criteria was based on the needs of the California fresh fruit market and was optimized for the summer planting for targeted production ideotype.

Plants of the new variety differ from plants of the seed parent '15-097R' primarily in that the plants of 'Plared 19140' are adapted for summer planting using frigo plants and produce a fruit which is both lighter red and larger than those of '15-097R'. Plants of the new variety 'Plared 19140' differ from plants of the pollen parent '16-54R' in the position of its achenes, which sit inserted in the fruit, and in its increased production summer planting using frigo plants. The new variety differs from known variety 'Portola' mainly in the color and shape of the fruit. 'Plared 19140' presents fruit with light or medium red (sRGB 248, 86, 48) while Portola presents medium or dark red fruits (sRGB 228, 52, 12). The form of 'Plared 19140' is ovate (UPOV #4) in shape while 'Portola' is conical (UPOV #2).

BRIEF DESCRIPTION OF THE DRAWINGS

The accompanying photographic illustrations show the typical appearance of the new variety 'Plared 19140'. The colors are as nearly true as is reasonably possible in a color representation of this type. Colors in the photographs may differ slightly from the color values cited in the detailed botanical description which accurately describes the colors of the new plant.

DETAILED BOTANICAL DESCRIPTION

Figure 1:
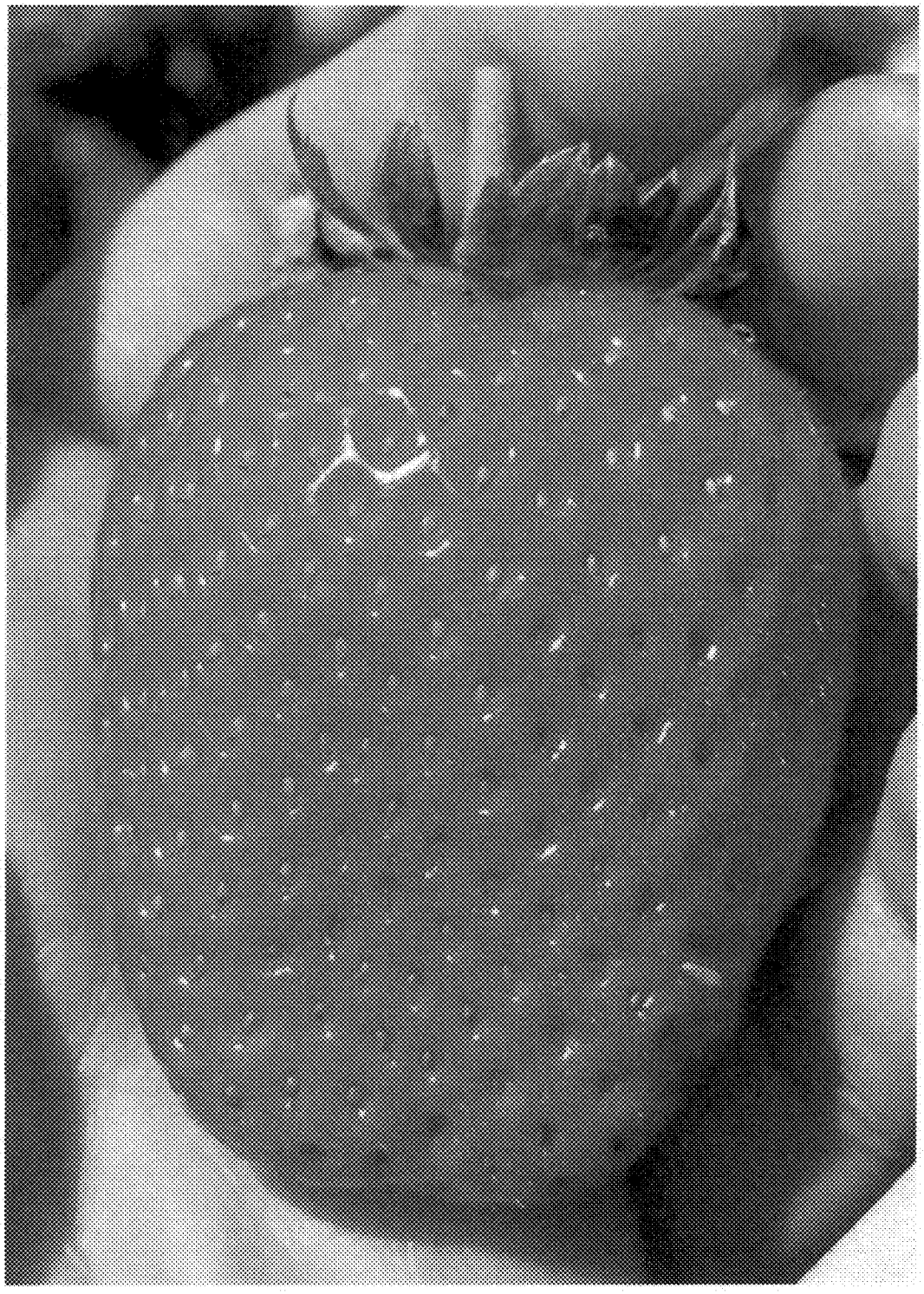
FIG. 1 is a photograph of the new variety 'Plared 19140', demonstrating its light red color, short, and insertion of its achenes.
Figure 2:
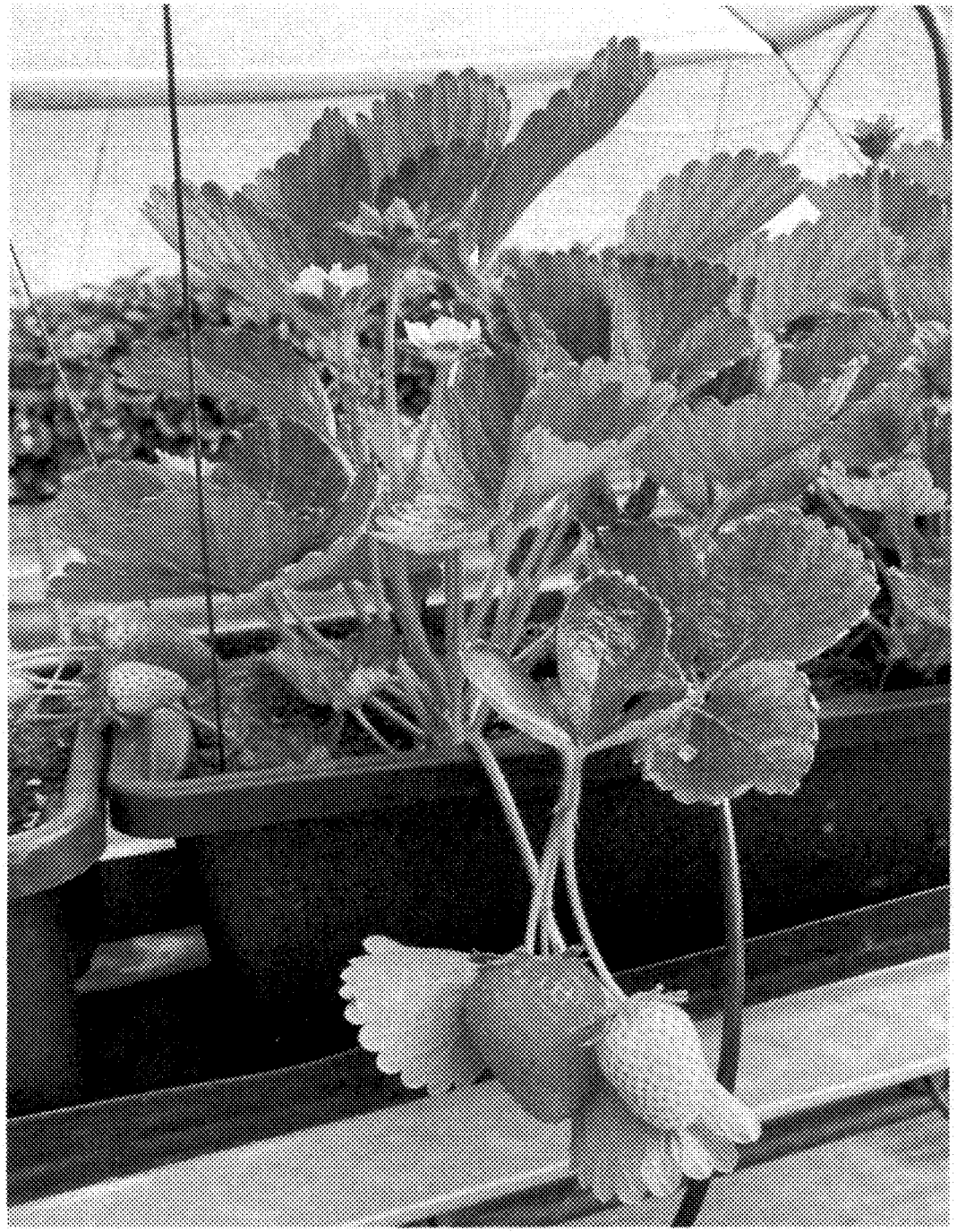
FIG. 2 is a photograph of new variety 'Plared 19140' at 3 months of age in hydroponic culture, demonstrating its exceptional pollination, short conical form, and low-density canopy.
Figure 3:
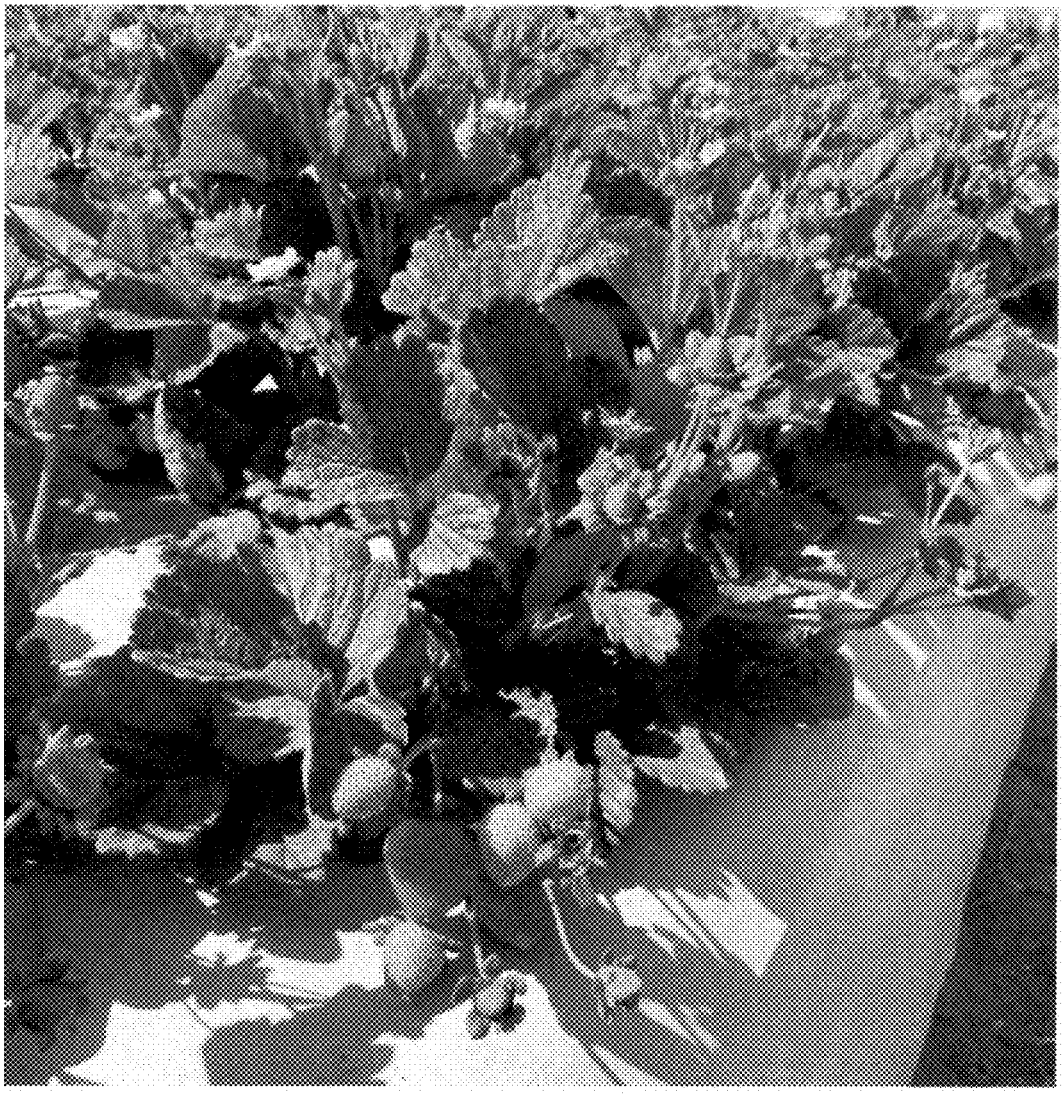
FIG. 3 is a photograph of new variety 'Plared 19140' at 3 months of age, demonstrating its adaptation for summer planting using frigo plants.
Figure 4:
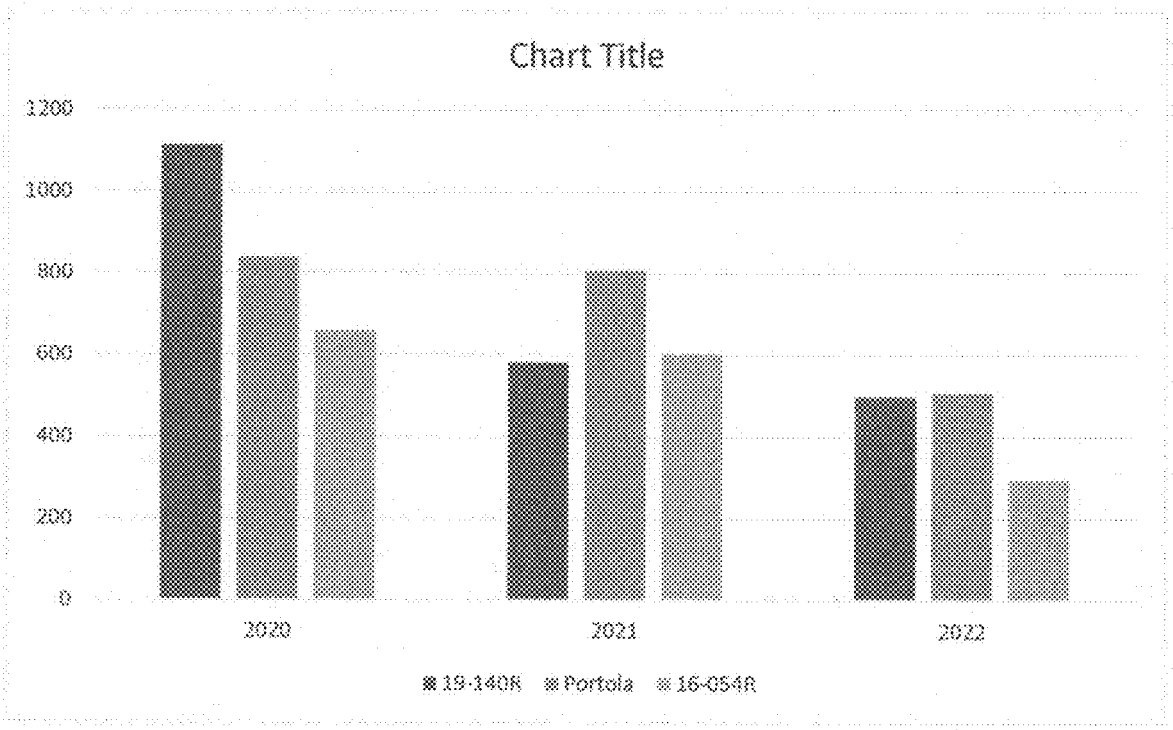
FIG. 4 is a bar graph of the new variety 'Plared 19140', its pollen parent 16-054R, and the industry reference 'Portola' (U.S. Plant Pat. No. 20,552).

The following detailed description sets forth the distinctive characteristics of 'Plared 19140'. The datum which defines these characteristics was collected from asexual reproductions of the original selection. Dimensions, sizes, colors, and other characteristics are approximations and averages set forth as accurately as possible. The plant history was taken on plants approximately 130 days after fall planting, and the descriptions relate to plants grown in Watsonville, California. Color notations are in reference to the standard RGB (sRGB) color space.

Classification:

a. *Family*.—Rosaceae.
b. *Botanical*.—*Fragaria*.
c. *Common name*.—Strawberry.
d. *Variety name*.—'Plared 19140'.

Parentage:

a. *Female parent*.—'15-097R'.
b. *Male parent*.—'16-54R'.

PLANT

General:

a. *Height*.—18 cm.
b. *Diameter*.—25 cm.
c. *Number of crowns per plant*.—5.
d. *Growth habit*.—Semi-upright.
e. *Density of foliage*.—Medium to low.
f. *Vigor*.—Medium.
g. *Stolon*.—i. Average number of daughter plants per sq. ft. — 12.

LEAVES

General:

a. *Number of leaflets*.—3.
a. *Color of upper surface*.—Medium Green (sRGB 0, 73, 5).
b. *Color of lower surface*.—Light Green (sRGB 95, 122, 69).
c. *Leaf blistering*.—Medium to strong.
d. *Leaf glossiness*.—Medium.
e. *Variegation*.—Absent.
f. *Terminal leaflet*.—i. Length — 7 cm. ii. Width — 6 cm. iii. Length/width ratio — 1.17. iv. Number of teeth/terminal leaflet — 22. v. Shape of base — Round to Obtuse. vi. Margin — More crenate than serrate. vii. Shape in cross section — Concave.
g. *Petiole*.—i. Length — 11.5 cm. ii. Diameter — 0.5 cm. iii. Attitude of hairs — Outward. iv. Bract frequency (number present on each petiole) — Absent. v. Color — Light Green (sRGB 129, 139, 84).
h. *Petiolule*.—i. Length — 0.5 cm. ii. Diameter — 0.3 cm. iii. Color — Light Green (sRGB 129, 139, 84).
i. *Stipule*.—i. Length — 2 cm. ii. Width — 1 cm. iii. Anthocyanin coloration — Weakly present, concentrated at margins. iv. Anthocyanin color — Light Red (sRGB 235, 98, 164). v. Stipule color — Light Green (sRGB 142, 144, 121) with Light Red (sRGB 235, 98, 164) concentrated at the margins.

INFLORESCENCE

General:

a. *Position in relation to foliage*.—Level to slightly above.
b. *Pedicel*.—i. Attitude of hairs — Outward. ii. Color — Light Green (sRGB 129, 139, 84).

*Flower*.—i. Flower diameter (petal tip to petal tip on non-flattened flower) — 3 cm. ii. Arrangement of petals — Free to slightly overlapping. iii. Stamen — Present. iv. Stamen length (if present) — 0.5 cm. v. Number of stamens per flower (if present) — 30. vi. Anther color (if stamen is present) — Yellow (sRGB 240, 205, 30).

d. *Petal*.—i. Length — 1.5 cm. ii. Width — 1.2 cm. iii. Length/width ratio — 1.25. iv. Typical and observed petal number — 5. v. Color of upper side — White (sRGB 255, 255, 255). vi. Color of lower side — White (sRGB 255, 255, 255). vii. Base shape — Obtuse. viii. Apex shape — Rounded. ix. Margin — Rounded.
e. *Calyx*.—i. Diameter (sepal tip to sepal tip, measured on back flower) — 3 cm. ii. Color — Middle Green (sRGB 65, 90, 45). iii. Size of calyx in relation to corolla — Larger.
f. *Sepal*.—i. Length — 1.5 cm. ii. Width — 0.75 cm. iii. Typical and observed sepal number — 16. iv. Color of upper surface — Dark Green (sRGB 52, 63, 14).

v. Color of lower surface — Light Green. (sRGB 82, 123, 64). vi. Attitude of sepals — Outwards.

FRUIT

General:

a. *Fruit weight*.—29.2 grams per fruit.
b. *Shape*.—Conical.
c. *Differences in shape between primary and secondary fruit*.—Slight.
d. *Glossiness*.—Medium to Strong.
e. *Color*.—Light Red to Medium Red (sRGB 250, 60, 75).
f. *Evenness of fruit color*.—Even.
g. *Position of achenes*.—Inserted.
h. *Peduncle length*.—12 cm.
i. *Peduncle diameter*.—0.3 cm.
j. *Position of calyx attachment*.—Inserted.
k. *Color of flesh* (*excluding core*).—Light Red (sRGB 250, 60, 75).
l. *Color of core*.—Light Red (sRGB 250, 110, 120).
m. *Sugar content* (*as soluble solids in degrees brix*).—8.4%.
n. *Production*.—i. Flowering interval — Beginning approximately 2 weeks of planting in summer with frigo plants, continuous flowering thereafter. ii. Harvest interval — Beginning approximately 6 weeks after planting in summer with frigo plants, continuous harvest thereafter. iii. Type of bearing — Day-Neutral. iv. Productivity — Three-year average of 730.8 grams per plant produced within five months of summer planting using frigo plants (e.g., planting in early June and harvesting through October).
o. *Fruit length*.—5.4 mm.
p. *Fruit width*.—3.9 mm.

What is claimed is:

1. A new and distinct variety of strawberry plant named 'Plared 19140', as illustrated herein.

* * * * *